United States Patent [19]

Mechanic et al.

[11] Patent Number: 4,486,403
[45] Date of Patent: Dec. 4, 1984

[54] COMPOSITION FOR AND TREATMENT OF TEETH

[76] Inventors: Gerald Mechanic, 107B Bolinwood Apts., 500 Umstead Dr., Chapel Hill, N.C. 27514; Itzhak Binderman, 13 Fievel St., Tel-Aviv, Israel

[21] Appl. No.: 450,926

[22] Filed: Dec. 20, 1982

[30] Foreign Application Priority Data

Jan. 1, 1982 [IL] Israel ................................. 64700

[51] Int. Cl.³ ........................... A61K 7/16; A61K 7/22
[52] U.S. Cl. ................................ 424/54; 424/49
[58] Field of Search .................................. 424/49–58

[56] References Cited

U.S. PATENT DOCUMENTS

| | | | |
|---|---|---|---|
| 1,470,794 | 10/1923 | Andresen | 424/54 |
| 2,470,906 | 5/1949 | Taylor | 424/49 |
| 3,925,543 | 12/1975 | Donohue | 424/54 |
| 3,932,605 | 1/1976 | Vit | 424/54 |
| 3,932,608 | 1/1976 | Anderson et al. | 424/54 |
| 3,943,241 | 3/1976 | Anderson et al. | 424/54 |
| 3,991,107 | 11/1976 | Vit | 424/54 |
| 3,998,945 | 12/1976 | Vit | 424/54 |
| 4,213,961 | 7/1980 | Curtis et al. | 424/54 |
| 4,225,579 | 9/1980 | Kleinberg | 424/54 |
| 4,256,731 | 3/1981 | Curtis et al. | 424/54 |
| 4,269,822 | 5/1981 | Pellico et al. | 424/54 |

FOREIGN PATENT DOCUMENTS

| | | |
|---|---|---|
| 83486 | 7/1983 | European Pat. Off. |
| 2345998 | 10/1977 | France |

OTHER PUBLICATIONS

Barrett et al., CA. 75 #18675g (1971), Nisshin Flour CA 95 #78785r (1981).
Binderman CA. 99 #93533h (1983) of Eur. Pat. Appl. EP83486 (Cysteine & Ascorbic Acid in Bread), Jul. 13, 1983.
Tamura et al., CA. 97 #138623g (1982) (Penicillamine Stimulates Development of Caries).
Dayan et al., CA. 95 #126002g (1981) (Penicillamine Degenerates Periodontals).
Baker CA. 73 #86319c (1970) (Penicillamine Affects Periodontal Membrane).
Gardner et al., CA. 66 #103664s (1967) (Cysteine Protects Against Tooth Cementum Lathyrism).
Ohshima et al., CA. 98 #29173t (1983) (Cysteamine Affects Periodontium).
Saruta et al., CA. 97 #121476n (1982) (Cysteine Reduced Dental Caries, Ascorbic Acid Did Not).
Paunio et al. CA. 76 #125044t (1972) (Enzyme in Plaque Converts Cystine to Cysteine).
Tanzetich et al. CA. 75 #60888d (1971) (Cysteine, Cysteine, Me Mercaptan H₂S Putrefy in Saliva).

*Primary Examiner*—Shep K. Rose
*Attorney, Agent, or Firm*—Steinberg & Raskin

[57] ABSTRACT

The invention relates to compositions and treatments for inhibiting or eliminating the formation of dental caries. The composition comprises a dental carie inhibiting effective amount of a compound containing a thiol group or a disulfide group which compound acts as a collagenase inhibitor and a pharmaceutically acceptable carrier adapted to be applied to and maintained in contact with the teeth. In accordance with the invention this composition is applied to the teeth, the collagenase inhibitor acting to inhibit or even eliminate the formation of dental caries.

1 Claim, No Drawings

COMPOSITION FOR AND TREATMENT OF TEETH

BACKGROUND OF THE INVENTION

It is well known that dental caries is an infectious disease which results in the progressive destruction of both inorganic and organic tooth substance. The caries process is initiated by the interplay of microorganisms adhering to tooth surfaces and a carbohydrate substrate in contact with a susceptible tooth surface. The caries lesion invariably originates on the external surface of the enamel of erupted teeth or on the exposed cementum of root surfaces and the process then progresses centripetally deep into the dentin.

The dental caries starts with the production of acids as a result of fermentation of the carbohydrate substrate by the microorganisms. These acids result in demineralization of localized tooth tissue. Consequently, the destruction of hard tissues, such as enamel, dentin, cementum or bone starts with the dissolution of the inorganic material of these tissues, namely hydroxyapatite.

In the case of mature enamel this also results in the decomposition of the organic matrix since this constitutes only 2% of the total composition of the enamel. The situation is different in other hard tissues (dentin, cementum and bone) which consists of highly cross-linked collagen matrix which is resistant to degradation under conditions capable of causing demineralization of these tissues (weak acids or calcium-chelating agents).

Native collagen is resistant to general proteolytic digestion under physiological conditions (e.g. by proteolytic enzymes such as trypsin and chemotrypsin) due to its triple polypeptide helix structure. However, collagen can be cleaved by tissue collagenases into two large fragments which can then be further cleaved by non-specific peptidases.

We have found in studies which we have made that dentin material derived either from carious teeth or from intact teeth (human) contains collagenolytic activity, the carious dentin being significantly more active. This fact would appear to indicate that during the tooth development there is produced, besides the collagen, also collagenase in an inactive form, which may become activated in the course of the carious process and is consequently capable of degrading the collagen matrix of the dentin. Thus, we have found that practically the entire collagenolytic activity in the process of the carious disease originates from the collagenase of the dentin itself, although it is known that some bacteria involved in the carious process are capable of secreting collagenase enzymes of their own.

SUMMARY OF THE INVENTION

In accordance with the present invention a dental care composition is provided for the inhibition or elimination of the formation of dental caries, the composition comprising a dental carie inhibiting effective amount of at least one collagenase inhibitor which is a non-toxic compound containing a thiol group or thiol groups or a non-toxic compound containing a disulfide group or disulfide groups together with a pharmaceutically acceptable carrier which is adapted to be applied to and maintained in contact with the teeth.

The method of the present invention comprises the application to the teeth of a dental caries inhibiting effective amount of at least one collagenase inhibitor which is a non-toxic compound containing a thiol group or groups or a disulfide group or groups.

It is a primary object of the present invention to provide compositions which can be applied to the teeth to prevent and possibly eliminate the formation of dental caries.

It is another object of the present invention to provide a method of treating teeth to inhibit or prevent dental caries.

It is yet a further object of the present invention to provide compositions in any application form for application to and being placed in contact with the teeth for the purpose of inhibiting and possibly eliminating dental caries.

Other objects and advantages of the present will be apparent from a further reading of the specification and of the appended claims.

With the above and other objects in view, the present invention mainly comprises a dental caries inhibiting composition comprising a dental caries inhibiting effective amount of a non-toxic compound containing at least one thiol group or at least one disulfied group, together with a pharmaceutically acceptable carrier adapted to be applied to and maintained in contact with the teeth.

The non-toxic compounds may be in free form or in the form of a salt or in complex form.

It has been found that the collagenolytic activity of the carious dentin can be inhibited or entirely suppressed by the use of compounds which contain thiol groups, either in free form or in latent form, such as disulfides in the form of metal salts of the thiol groups. The most preferred compound for the purposes of the present invention has been found to be cysteine.

In vivo experiments have shown, in accordance with the present invention that cysteine significantly inhibits the development of carious dentin lesions in rats fed on a cariogenic sugar diet.

Thus, the present invention provides dental care compositions for the inhibition or elimination of the formation of dental caries by the use of the collagenase inhibitors of the invention, such inhibitors being non-toxic compounds containing thiol groups in free form or in the form of a pharmaceutically acceptable salt or complex form, as well as non-toxic compounds containing disulfide groups. These collagenase inhibitors are dispersed in a pharmaceutically acceptable carrier adapted to be applied to the teeth and maintained in contact therewith.

The active collagenase inhibitors for use in accordance with the present invention are non-toxic aliphatic and aromatic monothiol and polythiol compounds, as well as salts and complexes of the thiol groups in such compounds with pharmaceutically acceptable cations such as alkali metal and alkaline earth metal salts.

The present invention further comprises for use as collagenase inhibitors aliphatic or aromatic disulfides, in which case the dental care compositions may optionally also include a suitable non-toxic reducing agent which is capable of reducing the disulfide group to form a pair of free thiol groups in situ. In addition it is possible in accordance with the present invention to provide a dental care composition comprising a disulfide compound plus an auxiliary preparation comprising a suitable reducing agent which may be applied to the teeth either separately or in sequence.

In accordance with the present invention it is possible to use as collagenase inhibitors either the chemical compounds themselves which contain the thiol groups or which can be reduced to contain thiol groups, (disulfide compounds) or to use the natural substances containing these compounds such as egg yolk, proteins and protein derivatives, such as hair protein derivatives, and extracts of garlic, onions, scallions, liiks, schallots and the like.

As indicated above, the preferred collagenase inhibitor for use in accordance with the present invention is cysteine.

The dental care compositions according to the invention, in particular those wherein the active ingredient comprises free thiol groups, may preferably further include a pharmaceutically acceptable anti-oxidant, for example vitamin C.

The novel compositions according to the invention are adapted for use both in personal everyday oral hygiene as dentifrices (e.g. tooth paste, mouth washes, tooth powder, etc.) and in dentistry. Among the main applications of the compositions in dentistry are the following:

1. sublining and lining of cavities;
2. cavity toilet with the compositions;
3. in indirect pulp capping;
4. in the filling of root canals;
5. for application of any natural abutment before cementation of a bridgework;
6. for application to resorption areas of bone, cementum or dentin;
7. as mouth rinses after periodontal treatment, including surgery.

The specific use for which a dental care composition according to the invention is adapted would determine the appropriate choice of the various parameters of the composition, namely the nature and concentration of the active collagenase inhibitor, the chemical nature and physical properties of the carrier, and the nature of any other additives present, selected from those conventionally used in compositions of this type.

Thus, oral hygiene compositions according to the invention for use as dentifrices should preferably contain the active collagenase inhibitor at a concentration corresponding to from about 1 to about 500 milli-equivalents of free or latent thiol group per liter of the preparation, more preferably from about 10 to about 100 milli-equivalents per liter. Thus, for example, when cysteine is used as the active inhibitor in a liquid dentifrice according to the invention, a suitable concentration would be 0.01 molar corresponding to about 0.16% by weight.

Oral hygiene compositions according to the invention for use as dentifrices, may be in the form of powders, pastes or liquids. In addition to the collagenase inhibitors according to the invention these dentifrices will usually also contain conventional substances. Thus, for example, in a toothpaste there will be incorporated abrasive and/or polishing materials such as calcium carbonate, dicalcium phosphate, calcium phosphate, calcium sulfate or various forms of silica; surfactants, such as sodium lauryl sulfate or sodium dodecylbenzene-sulfonate; gelling agents (or thickeners) such as natural and synthetic gums and gum-like materials, e.g. carboxymethyl cellulose, tragacanth, guar or starch; flavouring and/or natural or synthetic sweetening agents, such as saccharin, flavouring oils (e.g. oils of spearmint, peppermint, wintergreen); and other excipients, such as colouring or whitening agents (e.g. titanium dioxide), preservatives (e.g. sodium benzoate), emulsifying agents and acidifying agents (e.g. phosphoric or citric acid).

Dental care compositions according to the invention in the form of tooth powders and pastes are prepared in the usual manner by mixing the constituents in the dry state or as slurries or solutions.

In general the liquids in the cental pastes or mouth washes in accordance with the invention will comprise primarily water, glycerol, sorbitol or propylene glycol or suitable mixtures of any of these liquids. A mixture of water and glycerol, probably in combination with sorbitol, can be advantageously used.

DESCRIPTION OF THE PREFERRED EMBODIMENTS

The following examples are given to further illustrate the present invention. The scope of the invention is not, however, meant to be limited to the specific details of the examples.

In the following examples all quantities are expressed on a weight basis.

EXAMPLE I

A tooth paste is prepared of the following composition:

| Precipitated silica (e.g. Neosyl) | about 23% |
|---|---|
| Paraffin | 15% |
| PAB-esters | 0.2% |
| Methylcellulose | 1.8% |
| Aromatic substances | 2% |
| Cysteine | 0.15% |
| Distilled water | up to 100% |

Application of this tooth paste in the same manner as in the case of any other tooth paste results in reduction in the number of dental caries.

The same results are achieved with the tooth pastes, tooth powders, mouth washes, etc. of the following examples:

EXAMPLE II

| Tooth Paste | |
|---|---|
| Calcium carbonate | 50% |
| Tricalcium phosphate | 5% |
| Sorbitol (70% solution) | 10% |
| Glycerol | 20% |
| Tragacanth | 2% |
| Aromatic substances | 0.8% |
| Cysteine | 0.2% |
| PAB-esters | 0.1% |
| Distilled water | up to 100% |

EXAMPLE III

| Tooth Paste | |
|---|---|
| Aluminium-hydroxide | 40% |
| Na—fluoride | 0.1% |
| Sorbitol (70% solution) | 25% |
| Glycerol | 5% |
| Aromatic substances | 1.2% |
| Na—alginate | 1% |
| PAB-esters | 0.1% |
| Saccharine | 0.25% |
| Cysteine | 0.2% |
| Water | up to 100% |

EXAMPLE IV

| Tooth Powder | |
| --- | --- |
| Cysteine | 0.3% |
| Aromatic substances | 2% |
| Na—cyclamate | 0.5% |
| Detergent (Texapon L 100) | 1% |
| Calcium phosphate | up to 100% |

EXAMPLE V

| Mouth Wash | |
| --- | --- |
| Methylcellulose (low viscous) | 1% |
| Aromatic substances | 1% |
| PAB-esters | 0.15% |
| Dinatrium phosphate 0 aq. | 1.5% |
| Citric acid 1 aq. | 1.0% |
| Cysteine | 0.2% |
| Distilled water | up to 100% |

EXAMPLE VI

| Tooth Powder | |
| --- | --- |
| Na—cyclamate | 0.75% |
| Aromatic substances | 2.25% |
| Cysteine | 0.3% |
| Tricalcium phosphate | up to 100% |

EXAMPLE VII

| Tooth Powder | |
| --- | --- |
| Aromatic substances | 1% |
| Na—fluoride | 0.1% |
| Detergent | 1% |
| Cysteine | 0.2% |

| Tooth Powder (continued) | |
| --- | --- |
| Na—saccharine | 0.25% |
| Micro-cystalline aluminium hydroxide | up to 100% |

EXAMPLE VIII

Jet-stream teeth cleaner

To the water to be used in the conventional apparatus to deliver a high velocity jet of water there is added cysteine in the amount of 2.5 g per liter.

Although cysteine has been given as the most preferred collagenase inhibitor, the invention is equally applicable to the use of other thiol group-containing or disulfide group-containing compounds, including penicillamine, homocysteine, cysteamine, cystamine and their acyl derivatives such as acetyl and propanyl as well as amino acyl derivatives thereof. Also suitable are mercaptoethanol and its ethyl ester, mercaptoacetic acid ethyl ester and acyl derivatives thereof. It is also suitable to use cysteine plus a reducing agent such as ascorbic acid or ascorbate salts or homocystine plus a reducing agent such as ascorbic acid and its salts.

While the invention has been illustrated with respect to specific dental care compositions, it is apparent that variations and modification of the invention can be made without departing from the spirit or scope of the invention.

What is claimed is:

1. Method for the inhibition or elimination of the formation of dental caries, which comprises the steps of
    applying to the teeth to be treated, a collagenase-inhibiting effective amount essentially of cysteine in free form or in the form of a pharmaceutically acceptable salt or complex, and
    allowing said collagenase-inhibiting effective amount of cysteine to contact the teeth for a time sufficient to act on the teeth and inhibit the action of collagenase, thereby preventing the formation of dental caries.

* * * * *